US00PP21481P2

(12) United States Plant Patent

Bergman

(10) Patent No.: US PP21,481 P2

(45) Date of Patent: Nov. 16, 2010

(54) *CHRYSANTHEMUM* PLANT NAMED 'YOSANTA CRUZ'

(50) Latin Name: *Chrysanthemum×morifolium*
Varietal Denomination: Yosanta Cruz

(75) Inventor: Wendy R. Bergman, Lehigh Acres, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/587,474

(22) Filed: Oct. 7, 2009

(51) Int. Cl.
*A01H 5/00* (2006.01)

(52) U.S. Cl. ..... Plt./286

(58) Field of Classification Search ..... Plt./286
See application file for complete search history.

*Primary Examiner*—Kent L Bell
(74) *Attorney, Agent, or Firm*—S. Matthew Edwards

(57) ABSTRACT

A new *Chrysanthemum* plant named 'Yosanta Cruz', particularly distinguished by the single-type inflorescence with bright orange-red and yellow bi-colored ray florets, vigorous and upright habit, uniform habit and flowering response, and good floriferousness.

1 Drawing Sheet

Latin name of the genus and species of the plant claimed: *Chrysanthemum×morifolium.*

Varietal denomination: 'Yosanta Cruz'.

BACKGROUND OF THE NEW PLANT

The present invention comprises a new *Chrysanthemum*, botanically known as *Chrysanthemum×morifolium*, and hereinafter referred to by the variety name 'Yosanta Cruz'.

'Yosanta Cruz' is a product of a planned breeding program. The new cultivar has single-type inflorescences with bright orange-red and yellow bi-colored ray florets, vigorous and upright habit, uniform habit and flowering response, and good floriferousness.

'Yosanta Cruz' originated from a hybridization made in January 2004 in a controlled breeding environment in Salinas, Calif. The female parent was the proprietary plant designated 'YB-A7399', unpatented, with daisy inflorescence form, medium bronze with yellow ray florets that twist with age.

The male parent of 'Yosanta Cruz' was a proprietary, unpatented plant identified as 'YB-A7002' with smaller inflorescence size, less vigorous growth, and about a one week later flowering response.

'Yosanta Cruz' was selected as one flowering plant within the progeny of the stated cross in December, 2005 grown out doors in a field covered by saran in Fort Myers, Fla.

The first act of asexual reproduction of 'Yosanta Cruz' was accomplished when vegetative cuttings were propagated from the initial selection in March 2006, in a controlled environment in Fort Myers, Fla.

A Plant Breeder's Right for this cultivar was applied for in Canada in March 2009. 'Yosanta Cruz' has not been made publicly available more than one year prior to the filing of this application.

BRIEF SUMMARY OF INVENTION

Horticultural examination of plants grown from cuttings of the plant initiated in March 2006, and continuing thereafter, has demonstrated that the combination of characteristics as herein disclosed for 'Yosanta Cruz' are firmly fixed and are retained through successive generations of asexual reproduction.

'Yosanta Cruz' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety:

1. Single-type inflorescences with bright orange-red and yellow bi-coloredray florets.
2. Vigorous and upright habit.
3. Uniform habit and flowering response.
4. Good floriferousness.

BRIEF DESCRIPTION OF THE PHOTOGRAPHS

The accompanying photographic drawing shows typical flower and foliage characteristics of 'Yosanta Cruz' with colors being as true as possible with an illustration of this type. The photographic drawing shows four flowering potted plants of the new variety growing in a 5-inch pot, and a close-up of the inflorescences.

DETAILED BOTANICAL DESCRIPTION

The plant descriptions, measurements were taken in Gilroy, Calif. in April 2009 under greenhouse conditions. These plants were started and grown in central coastal California, then shipped to Gilroy, Calif. in April 2009. Plants were grown under conditions which approximate those generally used in commercial potted *chrysanthemum* production and were about 10-11 weeks of age. The aforementioned photographs were taken in Salinas, Calif. under a covered patio in April, 2009.

Color references are made to The Royal Horticultural Society Colour Chart (R.H.S.) 2001.

TABLE 1

DIFFERENCES BETWEEN THE NEW VARIETY 'YOSANTA CRUZ' AND A SIMILAR VARIETY

| | 'Yosanta Cruz' | 'Cedar Falls' (U.S. Plant Pat. No. 13,068) |
|---|---|---|
| Ray floret color: | Deeper, darker red | Medium red |
| Flowering response: | 8 weeks | 9 weeks |
| Growth habit: | Vigorous | More compact |

Plant:

*Form, growth and habit.*—Herbaceous pot-type, vigorous and upright habit, freely branching, uniform habit and flowering response. Suitable for production- center budded or no bud removal.

*Plant height.*—20-22 cm.

*Plant height (inflorescence included).*—23-26 cm.

*Plant width.*—24-28 cm.

Roots:

*Number of days to initiate roots.*—4 days at about 22 degrees C.

*Number of days to produce a rooted cutting.*—10 days at 22 degrees C.

*Type.*—Fine, fibrous, free branching.

*Color.*—RHS N155B but whiter.

Foliage:

*Arrangement.*—Alternate, simple.

*Immature, leaf color, upper surface.*—Closest to RHS 147A.

*Lower surface.*—RHS 147B.

*Mature, leaf color, upper surface.*—Closest to RHS 147A but a little lighter.

*Lower surface.*—RHS 147B.

*Length.*—7.5-8.1 cm.

*Width.*—5.2-5.5 cm.

*Shape.*—Ovate.

*Base shape.*—Attenuate.

*Apex shape.*—Mucronulate.

*Margin.*—Palmately lobed; somewhat serrate.

*Texture, upper surface.*—Bi-fid T-shaped hairs.

*Lower surface.*—Bi-fid T-shaped hairs.

*Color of veins, upper surface.*—Closest to RHS 147B.

*Color of veins, lower surface.*—Closest to RHS 147B.

*Petiole color.*—Closest to RHS 147B.

*Length.*—1.7-2.1 cm.

*Diameter.*—0.2-0.25 cm.

*Texture.*—Bi-fid T-shaped hairs.

Stem:

*Quantity of main branches per plant.*—4-5.

*Quantity of leaves per branch.*—10-12.

*Color of stem.*—Between RHS 146A and RHS 146B.

*Length of stem.*—17-19 cm.

*Diameter.*—0.4 cm.

*Length of internodes.*—0.8-2.3 cm.

*Texture.*—Bi-fid T-shaped hairs.

*Color of peduncle.*—RHS 146B.

*Length of peduncle (cm).*—3.5-4.5 cm.

*Peduncle diameter (cm).*—0.2 cm.

*Texture.*—Bi-fid T-shaped hairs.

Inflorescence:

*Type.*—Composite type, solitary inflorescences, single type, borne terminally above foliage, ray florets arranged acropetally on a capitulum. Inflorescences do not totally lie flat.

*Quantity of short days to flowering (response time).*—52-56 days grown with center bud removal.

*Quantity of inflorescences per plant.*—13-20.

*Lastingness of individual blooms on the plant.*—28 days.

*Fragrance.*—Slight.

Bud (just before opening/showing color):

*Color.*—Closest to RHS N34A with RHS 6A at the apex.

*Length.*—1.5 cm.

*Width.*—0.7-0.8 cm.

*Shape.*—Oblate.

Immature inflorescence:

*Diameter.*—5.5-6.0 cm when flattened out.

*Color of ray florets, upper surface.*—Closest to RHS N34A with RHS 2A basally and RHS 3A at the apex.

*Lower surface.*—RHS 4A ground color; vertical striations of RHS 181B and darker margins, with RHS 4A at the apex.

Mature inflorescence:

*Diameter.*—7-8.5 cm.

*Total diameter of "disc".*—1.9-2.2 cm.

Ray florets:

*Average quantity of florets.*—27-29.

*Color of florets, upper surface.*—Closest to RHS 34A but a little lighter; RHS 2A basally; RHS 3A to RHS 3B at the apex

*Lower surface.*—RHS 4A ground color; vertical striations of RHS 181B and darker margins with RHS 4A at the apex.

*Length.*—3.8-4.0 cm.

*Width.*—0.8-0.95 cm.

*Shape.*—Oblong.

*Apex shape.*—Mostly obtuse.

*Margin.*—Entire.

*Texture, upper surface.*—Papillose.

*Lower surface.*—Papillose.

Disc florets:

*Average quantity of florets.*—About 200.

*Color of florets.*—RHS 9A.

*Length.*—0.6-0.7 cm.

*Width.*—0.1 cm.

*Shape.*—Tubular, enlongated.

*Apex shape.*—Acute, 5 pointed.

Phyllaries:

*Quantity.*—18-20.

*Color, upper surface.*—RHS 147B.

*Lower surface.*—RHS 147B.

*Length.*—0.5-0.7 cm.

*Width.*—0.1-0.2 cm.

*Shape.*—Lanceolate.

*Apex shape.*—Acute to obtuse.

*Based.*—Fused.

*Margins.*—Entire and slightly papery.

*Texture, upper surface.*—Glossy and smooth.

*Lower surface.*—Bi-fid T-shaped hairs.

Reproductive organs:

*Pistil.*—1.

*Length.*—0.6 cm.

*Style color.*—RHS 1C.

*Style length.*—0.4-0.5 cm.

*Stigma color.*—RHS 9B.

*Stigma shape.*—Bi-parted.

*Ovary color.*—RHS N155C.

*Stamens.*—4.

*Color of filaments.*—RHS 144B but slightly translucent.

*Length filaments.*—0.2-0.3 cm.

*Anther color.*—RHS 9B.

*Anther length.*—0.1 cm.

*Anther shape.*—Oblong.

*Color of pollen.*—RHS 9A.

*Pollen amount.*—Scarce.

*Fertility/seed set.*—Has not been observed on this hybrid.

Disease/pest resistance: Disease resistance or susceptibility has not been observed on this hybrid.

What is claimed is:

1. A new and distinct variety of *Chrysanthemum* plant named 'Yosanta Cruz', substantially as illustrated and described herein.

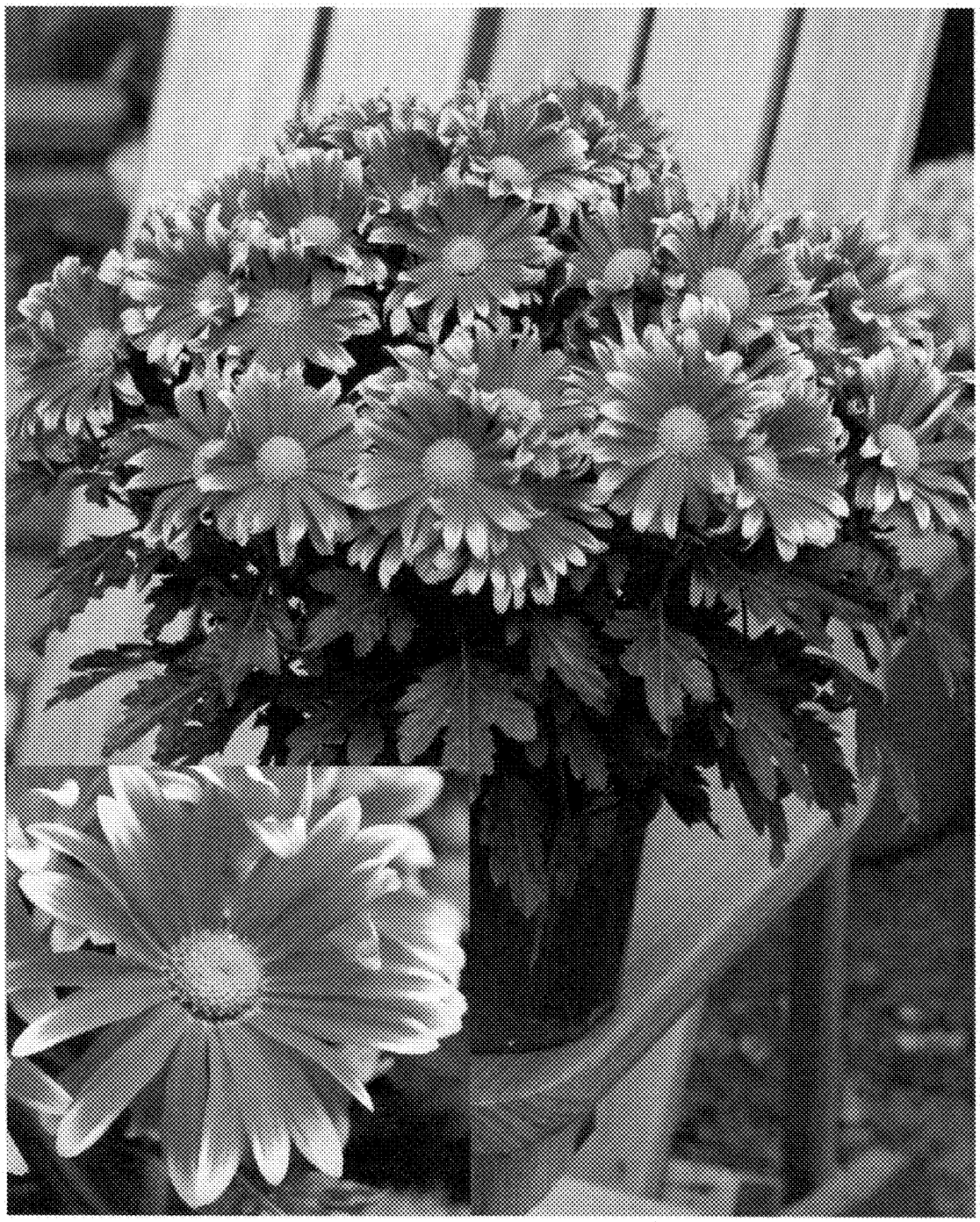

* * * * *